United States Patent [19]
Higgins

[11] Patent Number: 5,380,547
[45] Date of Patent: Jan. 10, 1995

[54] METHOD FOR MANUFACTURING TITANIUM-CONTAINING ORTHOPEDIC IMPLANT DEVICES

[76] Inventor: Joel C. Higgins, R.R. 1, Box 55, Claypool, Ind. 46510

[21] Appl. No.: 216,116

[22] Filed: Mar. 21, 1994

Related U.S. Application Data

[63] Continuation of Ser. No. 804,154, Dec. 6, 1991, abandoned.

[51] Int. Cl.$^6$ .................. A61F 2/28; B05D 3/06; C23C 14/02
[52] U.S. Cl. .................. 427/2.26; 427/576; 427/309; 623/16; 204/192.32
[58] Field of Search .............. 427/2.26, 576, 309; 623/16; 204/192.32

[56] References Cited

U.S. PATENT DOCUMENTS

| | | | |
|---|---|---|---|
| 4,460,415 | 7/1984 | Korhonen et al. | 148/222 |
| 4,790,851 | 12/1988 | Suire et al. | 623/16 |
| 4,793,871 | 12/1988 | Dawes et al. | 148/230 |
| 4,855,026 | 8/1989 | Sioshansi | 204/192.11 |
| 5,152,795 | 10/1992 | Sioshansi et al. | 623/16 |
| 5,192,323 | 3/1993 | Shetty et al. | 623/16 |
| 5,211,768 | 5/1993 | Priesser et al. | 148/230 |

OTHER PUBLICATIONS

Brochure from Nippon Denshi Kogyo Co. entitled: "Ion Nitriding Equipment: Ion-Nite": (dated prior to Dec. 90).

Rie, "Current Status of Plasma Diffusion Treatment Technique and Trends in New Application", ASM 2nd International Conference on Ion Nitriding/Carbonization, Cincinnati, Ohio (Sep. 8–20, 1989).

Williams et al, "Improvement in Wear Performance of Surgical Ti-6Al-4V Alloy by Ion Implantation of Carbon or Nitrogen" ASM 1st National Conference on the Applications of Ion Plating and Implantation to Materials, Atlanta, Ga. (Jun. 3–5, 1985).

Kembalyan et al., "Ion Nitriding of Titanium and Ti--6Al-4V Alloy", ASM 2nd International Conference on Ion Nitriding/Carbonization, Cincinnati, Ohio (Sep. 8–20, 1989).

Primary Examiner—Shrive Beck
Assistant Examiner—Bret Chen
Attorney, Agent, or Firm—Harness, Dickey & Pierce

[57] ABSTRACT

A method for treating orthopedic implants subject to wear and fatigue, and an orthopedic implant device treated in accordance with the described method. The orthopedic implant device is initially located in a reaction vessel. The outer surface of the orthopedic implant device is then subject to plasma nitriding so as to form a nitrogen enriched layer on the outer surface of the orthopedic implant device.

10 Claims, 2 Drawing Sheets

METHOD FOR MANUFACTURING TITANIUM-CONTAINING ORTHOPEDIC IMPLANT DEVICES

This is a continuation of U.S. patent application Ser. No. 07/804,154, filed Dec. 6, 1991, now abandoned.

BACKGROUND OF THE INVENTION

The present invention relates generally to the treatment of orthopedic implant devices, and more particularly, to a surface treatment applicable to such devices in which the wear resistant properties of orthopedic implant devices are enhanced while the fatigue strength is maintained.

More specifically, the present invention relates to orthopedic implant devices which are often used by surgeons to replace or repair bones and joints which have either been fractured or have degenerated. Examples of such orthopedic implant devices are disclosed in U.S. Pat. No. 4,864,608 which describes a hip prosthesis in which the surface treatment process of the present invention is applicable. The present invention may also be applicable to other orthopedic implant devices such as knee and shoulder prostheses, as well as other types of orthopedic implants which are subject to wear and fatigue.

Representative of the functions of many different types of orthopedic implant devices, the hip prosthesis disclosed in U.S. Pat. No. 4,864,608 is used to replace a natural hip which has degenerated. The hip prosthesis includes a stem which is inserted into and supported by the femur, as well as a projecting ball which is designed to fit within the acetabular socket of the patient receiving the implant. Because the hip prosthesis is under relatively high stress during usage, the hip prosthesis may experience wear for a variety of reasons.

It is generally known that surface treatment of orthopedic implant devices may improve wear characteristics. For example, ion implantation is used to place a nitrogen-enriched layer on the surface of orthopedic implant devices. Because such orthopedic implant devices are typically formed from a titanium-based material, the resulting titanium nitride layer creates a wear resistant surface layer. Physical vapor deposition is also used to create a wear resistant layer on orthopedic implant devices. When using physical vapor deposition, metal is evaporated and then condensed on the surface of the orthopedic implant device so as to form a wear resistant coating.

While these processes are generally successful in improving the wear resistance characteristic of orthopedic implant devices, such processes often have several disadvantages. For example, the ion implantation technique is effectively a "line of sight" procedure which makes it difficult to treat portions of orthopedic implant devices which have relatively irregular contours. When physical vapor deposition is used, the resulting titanium nitride coating may not be sufficiently supported by the substrate so that the coating may be relatively easily damaged when structure underlying the layer is subject to minor deformation. Furthermore, if the coating is cracked due to deformation of the underlying substrate, the crack may tend to propagate into the underlying substrate. Finally, because both ion implantation and physical vapor deposition techniques use relatively small batch sizes and are costly processes, the per unit cost of treating orthopedic implant devices using these techniques is relatively large.

While not generally used with orthopedic implant devices, plasma diffusion is also a known method for improving the wear characteristics of materials. In such a process, the material undergoing plasma diffusion is heated to relatively high temperatures (approximately 900° C.). However, this process is presumably believed to be undesirable for use in orthopedic implant devices for several reasons.

First, plasma diffusion is believed to reduce the fatigue strength of the material from which the orthopedic implant device could be formed. Second, the typical plasma diffusion technique often uses thermocouples to control processing. Such thermocouples are often located within the body of the article to be treated and therefore may not provide a relatively accurate indication of the temperature of the outer surface of the article per se. This is of particular concern with titanium-based articles which are not generally good thermal conductors and therefore the temperature at the surface of the article may be much different than the temperature at a position below the surface. Because such thermocouples are often not capable of accurately determining the surface temperature of article being processed, plasma diffusion processing often did not produce consistently uniform wear resistant surface layers on titanium.

SUMMARY OF THE INVENTION

Generally, the present invention provides a method for manufacturing an orthopedic implant device wherein the wear resistance properties of the device are enhanced while the fatigue strength of the device is maintained. The invention also encompasses orthopedic implant devices fabricated in accordance with the claimed method.

More specifically, the method of the present invention enhances the wear resistance properties of orthopedic implant devices, while maintaining a relatively high fatigue strength, by plasma nitriding the outer surface of the orthopedic implant device. In one aspect of the invention, plasma nitriding the outer surface of the orthopedic implant device occurs at a temperature preferably between approximately 600° C. and 730° C. In another aspect of the present invention, an initial step of cleaning the outer surface of the orthopedic implant device occurs by sputtering the outer surface of the orthopedic implant device.

An advantage of the method of the present invention is that orthopedic implant devices having improved wear resistant properties are possible as the result of using the method on the outer surface of these orthopedic implant devices.

Another advantage of the method of the present invention is that it is possible to maintain a relatively high fatigue strength of an orthopedic implant device while increasing the wear resistant properties of the device.

A further advantage of the present invention is that a wear resistant layer is able to be formed in areas of an orthopedic implant device which are not easily accessible to other types of surface treatment processes.

Another advantage of the method of the present invention is that adhesion between the bone cement and the orthopedic implant device is improved.

The invention, in one form thereof, provides a method of manufacturing an orthopedic implant device having an outer surface with enhanced wear resistant properties. The method includes several essential steps, including an initial step of locating the orthopedic implant device in a reaction vessel. According to a further step of the invention, plasma nitriding then occurs on the outer surface of the orthopedic implant device so as to form a nitrogen enriched layer on the outer surface.

The invention further provides, in one form thereof, a method of increasing the wear resistance of an orthopedic implant device having a titanium outer surface. The outer surface of the orthopedic implant device is first cleaned. Next, the temperature of the outer surface of the orthopedic implant device is raised to within a temperature range which substantially maintains the fatigue strength of the orthopedic implant device. After the temperature of the outer surface of the orthopedic implant device is raised to within this temperature range, the titanium containing outer surface is exposed to a nitrogen enriched environment so as to form a nitrogen enriched layer on the orthopedic implant device.

DESCRIPTION OF THE PREFERRED EMBODIMENT

Figure 1:
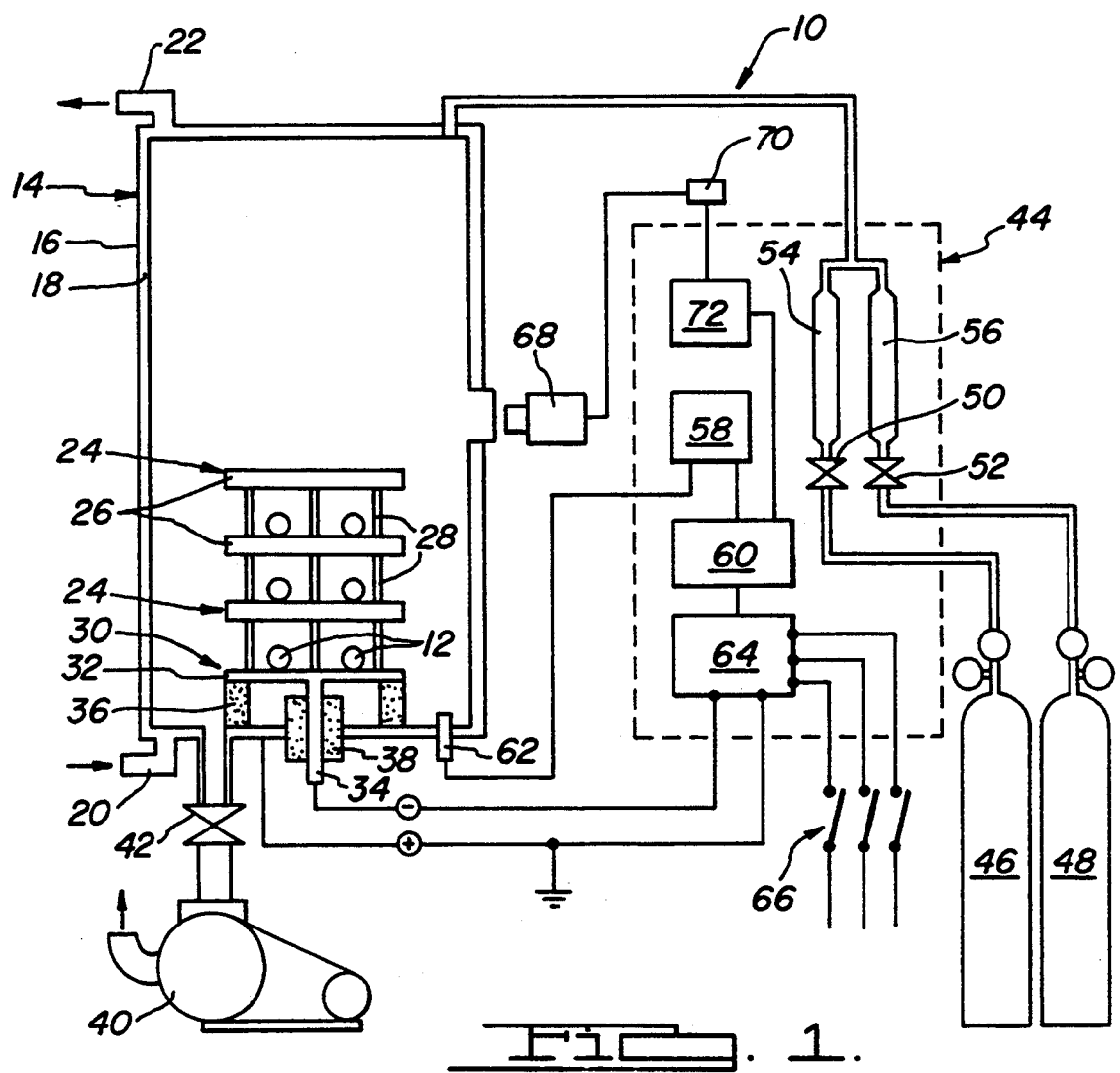
FIG. 1 is a diagrammatic illustration of the apparatus of the type used in accordance with the teachings of the preferred method of the present invention.

Referring now to FIG. 1, there is shown a plasma diffusion apparatus 10 of the type used in carrying out the method for producing an orthopedic implant device 12 in accordance with the preferred embodiment of the present invention. The orthopedic implant device 12 is in the form of a hip stem which is implanted to replace the natural hip after it has degenerated. It will be understood, however, that other types of orthopedic implant devices may also be used in connection with the present invention such as knee or shoulder prostheses. In addition, the orthopedic implant device 12 may typically be made out of Ti-6Al-4V. However, other suitable materials may be used such as $Ti_6Al_7Nb$ and commercially pure titanium.

The plasma diffusion apparatus 10 includes a reaction vessel 14 which houses a plurality of orthopedic implant devices 12 upon which a nitrogen-enriched surface layer having improved wear resistant properties is to be formed. The reaction vessel 14 has the wall structure 16 which is electrically grounded as shown in FIG. 1. The wall structure 16 includes a wall cavity 18 which is able to receive water from an inlet member 20 as well as permit water to be drained from the wall cavity 18 by an outlet member 22 thereby allowing water to circulate within the wall cavity 18. By circulating water within the wall cavity 18, the reaction vessel 14 may be cooled so as to permit the orthopedic implant devices 12 within the reaction vessel 14 to be maintained at a relatively low temperature.

Disposed within the reaction vessel 14 are a plurality of support fixtures 24 which are used to support a plurality of orthopedic implant devices 12. Each of the support fixtures 24 includes a disk-shaped member 26 as well as three leg members 28. The disk-shaped members 26 are used for providing a surface upon which a plurality of orthopedic implant devices 12 may be placed. The three leg members 28 of each of the support fixtures 24 extend downwardly from the lower surface of the disk-shaped member 26 and are operable to allow the support fixtures 24 to be stacked on top of one another. Because the support fixtures 24 are able to be stacked on top of one another, the orthopedic implant devices 12 located within the reaction vessel 14 are able to be located approximately the same distance from adjacent orthopedic implant devices 12. This orientation of orthopedic implant devices 12 permits a relatively uniform nitrogen enriched layer to be applied on each of the orthopedic implant devices 12. The support fixtures 24 are preferably made from Haynes alloy 230 which is relatively resistant to plasma or ion nitriding and that it is relatively strong at the desired operating temperatures.

Also disposed within the reaction vessel 14 is a hearth plate 30. The hearth plate 30 includes a disk-shaped upper portion 32 which provides a surface for supporting the support fixtures 24, as well as providing a support surface for additional orthopedic implant devices 12. Projecting downward from the lower surface of the disk-shaped upper portion 32 is a cylindrical member 34. The cylindrical member 34 extends downward through the wall structure 16 and electrically communicates with the gas supply and control module described below. The hearth plate 30 is electrically insulated from the reaction vessel 14 by a first annularly shaped insulating member 36 and a second annularly shaped insulating member 38. The first annularly shaped insulating member 36 extends from the lower surface of the disk-shaped upper portion 32 of the hearth plate 30 at its outer periphery to the bottom inner surface of the wall structure 16 of the reaction vessel 14. The second annular insulating member 38 extends from the lower surface of the disk-shaped upper portion 32 of the hearth plate 30 through the bottom surface of the wall structure 16 and is disposed adjacent to the cylindrical member 34 of the hearth plate 30. The first and second annularly shaped insulating members 36 and 38 are used to electrically insulate the wall structure 16 and the hearth plate 30 during the sputter cleaning and plasma nitriding steps described below.

Connected to the reaction vessel 14 is a vacuum pump 40 and a pump valve 42. The vacuum pump 40 is used for evacuating the reaction vessel 14 once a plurality of orthopedic implant devices 12 have been located within the reaction vessel 14. The pump valve 42 is used for controlling the connection between the reaction vessel 14 and the pump 40 so as to regulate the pressure of the gases within the reaction vessel 14.

As more fully described below, argon is initially introduced into the reaction vessel 14 during a sputter cleaning operation after which nitrogen is introduced so as to create a nitrogen enriched surface layer which includes titanium nitride on the orthopedic implant devices 12 located within the reaction vessel 14. To supply argon and nitrogen to the reaction vessel 14 as well as to control the temperature of the surfaces of the orthopedic implant devices 12 within the reaction vessel 14, a gas supply and control module 44 is provided. The gas supply and control module 44 is connected to a tank 46 which contains compressed argon gas and to a tank 48 containing liquid nitrogen. The gas supply and control module 44 in turn delivers the gases contained in the tanks 46 and 48 to the reaction vessel 14 in a regulated manner.

To regulate the flow of argon and nitrogen into the reaction vessel 14, the gas supply and control module 44 further comprises the valves 50 and 52 and the gas flow meters 54 and 56. The gas flow meter 54 is used for monitoring the amount of argon gas which is delivered from the tank 46 to the reaction vessel 14, while the valve 50 which is disposed between the gas flow meter 54 and the tank 46 is able to control the flow of argon from the tank 46 to the reaction vessel 14. Similarly, the gas flow meter 56 is used for monitoring the amount of nitrogen delivered to the reaction vessel 14, while the valve 52 which is disposed between the tank 48 and the gas flow meter 56 is used for controlling the amount of nitrogen delivered from the tank 48 to the reaction vessel 14.

To adjust the pressure of gases in the reaction vessel 14, the gas supply and control module 44 further comprises a pressure monitor 58 and a control unit 60. The pressure monitor 58 is connected to a pressure sensor 62 which is located within the reaction vessel 14. The output of the pressure sensor 62 is delivered to the pressure monitor 58 which provides a visual indication of the pressure within the reaction vessel 14. In addition, the output of the pressure sensor 62 is delivered to the control unit 60 through the pressure monitor 58. The control unit 60 is able to adjust the valves 42, 50 and 52 in the manner described below in response to the signal received from the pressure sensor 62 so as to control the flow of argon and nitrogen into the reaction vessel 14 as well as the pressure of the gases within the reaction vessel 14.

As those skilled in the art will appreciate, ionized nitrogen gas within the reaction vessel 14 will combine with the titanium within the orthopedic implant device 12 to form a nitrogen enriched surface layer containing titanium nitrides on the orthopedic implant device 12. To ionize the nitrogen within the reaction vessel 14, the gas supply and control module 44 further includes a power supply 64 which is controlled by the control unit 60. The power supply 64 receives energy from an external source (not shown) through the switches 66. The negative output of the power supply 64 is connected to the cylindrical member 34 of the hearth plate 30, while the positive output of the power supply 64 is grounded. Because the support fixtures 24 as well as the hearth plate 12 are electrically conductive, the orthopedic implant devices 12 located on the support fixtures 24 are at the same electrical potential as the hearth plate 30. Accordingly, when the appropriate voltage differential is generated between the hearth plate 30 and the wall structure 16 of the reaction vessel 14 by the power supply 64, nitrogen within the reaction vessel 14 ionizes and the nitrogen ions created thereby bombard the surface of the orthopedic implant devices 12 so as to form a nitrogen enriched surface layer on the orthopedic implant devices 12.

As the nitrogen within the reaction vessel 14 ionizes, the temperature within the reaction vessel 14 begins to increase. Because it is desirable to control the temperature within the reaction vessel 14 so as to maintain the fatigue strength of the orthopedic implant devices, the gas supply and control module 44 electrically communicates with a thermosensor 68. The thermosensor 68 is located outside the reaction vessel 14 and measures the infrared radiation emitted from the surface of the orthopedic implant devices 12 within the reaction vessel 14 so as to generate an output which is indicative of the surface temperature of the orthopedic implant device 12. By measuring the infrared radiation emitted from the surface of the orthopedic implant devices 12, the thermosensor 68 is able to accurately indicate the surface temperature of the outer surface of the orthopedic implant devices 12. This allows the plasma nitriding process to be relatively accurately controlled by the gas supply and control module 44. Accordingly, relatively uniform wear resistant layers may be formed on the orthopedic implant devices 12 and a relatively large number of orthopedic implant devices 12 (e.g., ninety-two devices) can be processed at one time thereby reducing per unit cost of the treatment. Preferably, the thermosensor 68 may be an optical pyrometer.

The output of the thermosensor 68 is delivered to a converter 70 which is operable to convert the output of the thermosensor 68 into a signal which may be used by a temperature monitor 72 as well as the control unit 60. The temperature monitor 72 allows a visual indication of the surface temperature of the orthopedic implant devices 12 within the reaction vessel 14. The control unit 60 in turn adjusts the current and voltage delivered to the hearth plate 30 so as to regulate the temperature within the reaction vessel 14 preferably between the range of 600° C. and 730° C. In doing so, the control unit 60 maintains the voltage differential between hearth plate 30 and the reaction vessel 14 in the range of between 400 and 600 volts. However, it is to be understood that temperatures down to 350° C. may be used though the processing time may be substantially longer.

Figure 2:
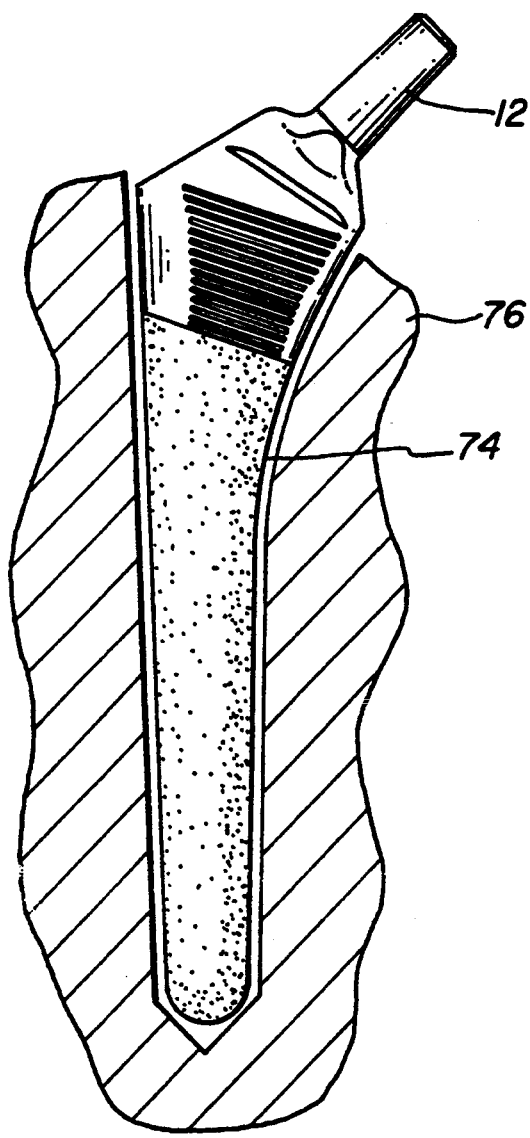
FIG. 2 is a sectional view of an orthopedic implant device manufactured in accordance with the teachings of the preferred method of the present invention shown in an operative relationship with respect to a femur.

Because the temperature of the outer surface of the orthopedic implant device 12 is maintained presumably between 600° C. and 730° C. during plasma nitriding, relatively low grain growth occurs within the orthopedic implant device 12. This results in several advantageous properties. First, there is little change in the fatigue strength of the orthopedic implant device 12 because grain growth is minimized. Accordingly, the formation of a wear resistant layer on the outer surface of the orthopedic implant device 12 is achieved while the fatigue strength of the orthopedic implant device 12 is maintained. For example, plasma nitriding at 700° C. for a period of 16 hours results in very little change in fatigue strength (from 88±7 ksi to 85±5 ksi), while plasma nitriding for 12 hours at 850° C. shows approximately a 30% reduction in fatigue strength. Furthermore, because plasma nitriding the orthopedic implant device 12 increases the surface energy of the outer surface of the orthopedic implant device 12, there is increased adhesion between the orthopedic implant device 12 and the bone cement 74 (shown in FIG. 2) which is used to secure the orthopedic implant device 12 to the femur 76.

Figure 3:
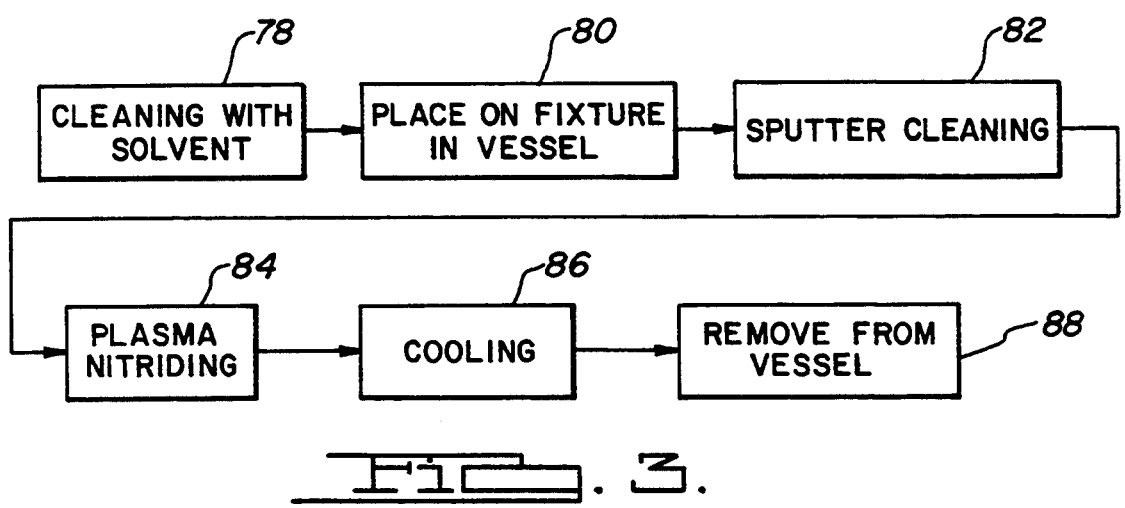
FIG. 3 is a diagrammatic representation of the process steps involved in an exemplary embodiment of the method of the present invention.

Referring now to FIG. 3, the steps for treating an orthopedic implant device 12 according to an exemplary embodiment of the present invention are diagrammatically illustrated. Generally, the block 78 represents the first step of cleaning the orthopedic implant device 12 with a solvent. The block 80 represents the next step of placing the orthopedic implant device 12 into the reaction vessel 14 after it has cleaned the solvent. The block 82 represents the next step of sputtering the outer surface of the orthopedic implant device 12. The block 84 represents the step of plasma nitriding the orthopedic implant device 12 in which a nitrogen enriched layer is formed on the outer surface of the orthopedic implant device 12. The orthopedic implant device 12 then undergoes cooling and then removal from the reaction vessel 14 as represented by the blocks 86 and 88 respectively. These steps will now be described in greater detail.

As represented by the block 78, the orthopedic implant device 12 is first cleaned with a solvent to remove organic contaminants which may be on the outer surface of the orthopedic implant device 12. This type of cleaning process may normally be done with solvents such as heptane or toluene in which the orthopedic implant device 12 is placed in a container containing such a solvent for a period of time and then is wiped clean with a lint free cloth. Once the orthopedic implant device 12 has been cleaned in this manner, any manual movement of the orthopedic implant device 12 is accomplished by using gloves so as to protect the surface of the orthopedic implant device 12 from contamination. Further, the orthopedic implant device 12 may also be temporarily stored in a protective plastic container to protect it from contamination if the orthopedic implant device 12 is not immediately placed in the reaction vessel.

Once a plurality of the orthopedic implant devices 12 have been cleaned with a solvent as represented by the block 78, the orthopedic implant devices 12 are placed on the support fixtures 24 within the reaction vessel 14 as represented by the block 80. As discussed above, the orthopedic implant devices 12 are located at approximately equally spaced intervals on the disk-shaped members 26 as well as the hearth plate 30 so as to permit a relatively uniform nitrogen enriched layer to be formed on each of the orthopedic implant devices 12. In addition, the disk-shaped member 26 of the uppermost support fixture 24 does not contain orthopedic implant devices 12 so that the nitrogen enriched layers formed on the orthopedic implant devices 12 are relatively uniform. Placement of the orthopedic implant devices 12 into the reaction vessel 14 is done in a manner such as by using gloves which is able to protect the orthopedic implant devices 12 from contamination.

The sputter cleaning step represented by the block 82 is then performed in the following manner. Once the orthopedic implant devices 12 are placed within the reaction vessel 14, the gas supply and control module 44 opens the pump valve 42 so as to allow the vacuum pump 40 to reduce the pressure within the reaction vessel 14 to approximately 50 microns. The gas supply and control module 44 then opens the valve 50 so as to cause argon from the tank 46 to backfill the reaction vessel 14. The gas supply and control module 44 then regulates the valve 50 as well as the pump valve 42 in such a manner so that the pressure within the reaction vessel 14 is approximately 500 microns under a relatively constant flow of nitrogen.

As this occurs, the voltage differential between the wall structure 16 and the hearth plate 30 of the reaction vessel 14 is slowly increased until the gas supply and control module 44 detects a relatively large voltage drop. Such a voltage drop indicates some of the remaining contaminants on the outer surface of the orthopedic implant devices 12 have been sputtered from the outer surface. The gas supply and control module 44 then maintains this voltage differential between wall structure 16 and the hearth plate 30 of the reaction vessel 14 until no further voltage drop occurs. The voltage differential between the wall structure 16 and the hearth plate 30 is again increased until the next relatively large voltage drop occurs indicating that further contaminants have been sputtered from the surface of the orthopedic implant devices 12. This process continues until the temperature of the outer surface of the orthopedic implant devices 12 are preferably within the range of between 600° C. and 730° C. When the temperature of the outer surfaces of the orthopedic implant devices 12 are within this range, the gas supply and control module 14 closes the valve 50 so no further argon is delivered from the tank 46 to the reaction vessel 14.

Following the sputter cleaning step represented by the block 82, the plasma nitriding step occurs as represented by block 84. The plasma nitriding step enriches the outer surface of the orthopedic implant device 12 by a combination of ion implantation of nitrogen ions into the surface of the orthopedic implant device 12 and by diffusion of nitrogen into the orthopedic implant device 12. In addition, the plasma nitriding step also enriches the outer surface of the orthopedic implant device 12 by sputtering titanium from the outer surface of the orthopedic implant device 12 and then depositing the titanium sputtered from the outer surface in combination with nitrogen onto the outer surface.

When the plasma nitriding step begins, the gas supply and control module 44 opens the valve 52 so that nitrogen from the tank 48 is delivered to the reaction vessel 14. The gas supply and control module 44 regulates the pressure of nitrogen within the reaction vessel 14 by controlling the pump valve 42 so that the pressure within the reaction vessel 14 is between 1000 and 10,000 microns. The higher pressures within this range are used with large components and components with holes, while lower pressures within this range are used by smaller components and components without holes. Furthermore, the gas supply and control module 44 regulates the voltage differential between the hearth plate 30 and the wall structure 16 of the reaction vessel 14 so as to maintain the temperature of the of the outer surface of the orthopedic implant devices 12 substantially within the range preferably between 600° C. and 730° C. for a period of between approximately 16 to 24 hours. By maintaining the temperature of the outer surfaces of the orthopedic implant devices within this range, the fatigue strength of the orthopedic implant device 12 is maintained. In addition, by maintaining the temperature of the outer surface of the orthopedic implant device 12 within this range for a relatively long period of time, the thickness of the titanium enriched layer is relatively large (e.g., exceeding 20 microns in thickness).

Once the plasma nitriding step represented by the block 84 has been completed, the reaction vessel 12 is cooled as represented by the block 86. During the step of cooling the reaction vessel 12, the gas supply and control module 44 closes the valve 52 so as to terminate delivery of nitrogen to the reaction vessel 14. At the same time, the gas supply and control module 44 eliminates the voltage differential between the wall structure 16 and the hearth plate 30 of the reaction vessel 14 until the outer surface of the orthopedic implant devices 12 reach ambient temperature. Alternatively, the gas supply and control module 44 may backfill the reaction vessel with argon to facilitate cooling of the outer surface of the orthopedic implant devices 12. Further, the gas supply and control module 44 may raise the voltage differential between the wall structure 16 and the hearth plate 30 of the reaction vessel 14 so as to sputter clean the outer surface of the orthopedic implant devices 12 as well as the inside of the reaction vessel 14. After this sputter cleaning process, the voltage differential between the hearth plate 30 and the wall structure 16 can be reduced so as to permit the orthopedic implant devices 12 to cool. The orthopedic implant devices 12 are then removed from the reaction vessel 14 as represented by the block 88.

A further understanding of the present invention will be had by reference to the examples set forth below for purposes of illustration but not for limitation. Each of these examples use a JIN-10S plasma diffusing apparatus available from Advanced Heat Treat Corp., Waterloo, Iowa, modified as set forth above.

EXAMPLE 1

Seventy-two tibial components for knee prostheses formed from Ti-6Al-4V are initially cleaned in a toluene wash. Of the 72 tibial components, 24 are placed on the hearth plate at substantially equally spaced intervals. In addition, 24 of the tibial components are placed on the disk-shaped member of the lowest support fixture while the remaining 24 tibial components are placed on the disk-shaped member associated with the middle support fixture. The reaction vessel is evacuated to a pressure of approximately 50 microns and then the reaction vessel is backfilled with argon. While the flow of argon into the reaction vessel remains relatively constant, the pressure within the reaction vessel is maintained at approximately 500 microns. The voltage differential between the hearth plate and the wall structure is increased over a four hour sputter cleaning period until the temperature of the outer surface of the tibial components is 600° C.

The flow of argon into the reaction vessel is terminated and then the flow of nitrogen into the reaction vessel is initiated. The temperature of the outer surface of the tibial components is maintained at approximately 600° C. while the pressure of nitrogen within the reaction vessel is held at approximately 1000 microns for 24 hours. The flow of nitrogen into the reaction vessel is terminated and the voltage differential between the hearth plate and the wall structure of the reaction vessel is reduced. The reaction vessel is then allowed to cool to ambient temperature and then the tibial components are removed.

A microhardness examination of the tibial components shows that a relatively thick nitrogen enriched layer is formed on the outer surface of the tibial components. In addition, fatigue testing of the tibial components shows that the fatigue strength of the tibial components is substantially unchanged.

EXAMPLE 2

Seventy-two tibial components for knee prostheses formed from Ti-6Al-4V are initially cleaned in a toluene wash. Of the 72 tibial components, 24 are placed on the hearth plate at substantially equally spaced intervals. In addition, 24 of the tibial components are placed on the disk-shaped member of the lowest support fixture while the remaining 24 tibial components are placed on the disk-shaped member associated with the middle support fixture. The reaction vessel is evacuated to a pressure of approximately 50 microns and then the reaction vessel is backfilled with argon. While the flow of argon into the reaction vessel remains relatively constant, the pressure within the reaction vessel is maintained at approximately 500 microns. The voltage differential between the hearth plate and the wall structure is increased over a four hour sputter cleaning period until the temperature of the outer surface of the tibial components is 640° C.

The flow of argon into the reaction vessel is terminated and then the flow of nitrogen into the reaction vessel is initiated. The temperature of the outer surface of the tibial components is maintained at approximately 640° C. while the pressure of nitrogen within the reaction vessel is held at approximately 1000 microns for 16 hours. The flow of nitrogen into the reaction vessel is terminated and the voltage differential between the hearth plate and the wall structure of the reaction vessel is reduced. The reaction vessel is then allowed to cool to ambient temperature and then the tibial components are removed.

A microhardness examination of the tibial components shows that a relatively thick (e.g., exceeding 20 microns) nitrogen enriched layer is formed on the outer surface of the tibial components. In addition, fatigue testing of the tibial components shows that the fatigue strength of the tibial components is substantially unchanged.

EXAMPLE 3

Seventy-two prosthetic hip stems formed from Ti-6Al-7Nb are initially cleaned in a heptane wash. Of the 72 hip stems, 24 are placed on the hearth plate at substantially equally spaced intervals. In addition, 24 of the hip stems are placed on the disk-shaped member of the lowest support fixture while the remaining 24 hip stems are placed on the disk-shaped member associated with the middle support fixture. The reaction vessel is evacuated to a pressure of approximately 50 microns and then the reaction vessel is backfilled with argon. While the flow of argon into the reaction vessel remains relatively constant, the pressure within the reaction vessel is maintained at approximately 500 microns. The voltage differential between the hearth plate and the wall structure is increased over a four hour sputter cleaning period until the temperature of the outer surface of the hip stems is equal to 700° C.

The flow of argon into the reaction vessel is terminated and then the flow of nitrogen into the reaction vessel is initiated. The temperature of the outer surface of the hip stems is maintained at 700° C. while the pressure of nitrogen within the reaction vessel is held at approximately 5000 microns for 16 hours. The flow of nitrogen into the reaction vessel is then terminated and the voltage differential between the hearth plate and the wall structure of the reaction vessel is reduced. Argon was then delivered to the reaction vessel so as to facilitate cooling of the reaction vessel. When the reaction vessel reaches ambient temperature, the reaction vessel is opened and the hip stems are removed.

A microhardness examination of the hip stems shows that a relatively thick (e.g., exceeding 20 microns) nitrogen enriched layer is formed on the outer surface of the hip stems. In addition, fatigue testing of the hip stems shows that the fatigue strength of the hip stems is substantially unchanged.

EXAMPLE 4

Seventy-two prosthetic hip stems with a tapered hole formed from Ti-6Al-4V are initially cleaned in a toluene wash. Of the 72 hip stems, 24 are placed on the hearth plate at substantially equally spaced intervals. In addition, 24 of the hip stems are placed on the disk-shaped member of the lowest support fixture while the remaining 24 hip stems are placed on the disk-shaped member associated with the middle support fixture. The reaction vessel is evacuated to a pressure of approximately 50 microns and then the reaction vessel is backfilled with argon. While the flow of argon into the reaction vessel remains relatively constant, the pressure within the reaction vessel is maintained at approximately 500 microns. The voltage differential between the hearth plate and the wall structure is increased over a four hour sputter cleaning period until the temperature of the outer surface of the hip stems is equal to 730° C.

The flow of argon into the reaction vessel is terminated and then the flow of nitrogen into the reaction vessel is initiated. The temperature of the outer surface of the hip stems is maintained at 730° C. while the pressure of nitrogen within the reaction vessel is held at approximately 10,000 microns for 16 hours. The flow of nitrogen into the reaction vessel is then terminated. Argon is then introduced into the reaction vessel and the voltage differential is created between the hearth plate and the wall structure to sputter clean the hip stems. The voltage differential between the hip stems and the wall structure is reduced and the reaction vessel allowed to cool to ambient temperature.

A microhardness examination of the hip stems shows that a relatively thick (e.g., exceeding 20 microns) nitrogen enriched layer is formed on the outer surface of the hip stem. In addition, fatigue testing of the hip stems shows that the fatigue strength of the hip stems is substantially unchanged.

It will be appreciated that the foregoing description of the preferred embodiment of the invention is presented by way of illustration only and not by way of any limitation, and that various alternatives and modifications may be made to the illustrative embodiment without departing from the spirit and scope of the invention.

I claim:

1. A method of manufacturing a titanium-containing orthopedic implant device having an outer surface with enhanced wear resistant properties, comprising the steps of:
   locating said orthopedic implant device in a reaction vessel;
   sensing the temperature of said outer surface of said orthopedic implant device;
   treating said outer surface of said orthopedic implant device to produce a wear resistant layer on said outer surface, said step of treating said outer surface of said orthopedic implant device by plasma nitriding said outer surface at a temperature below about 730° C.; and
   controlling the treatment of said outer surface of said orthopedic implant device at least partially in response to the temperature of said outer surface.

2. The method set forth in claim 1, wherein said step of sensing the temperature of said outer surface of said orthopedic implant device includes the step of using an optical pyrometer to measure the temperature of said outer surface.

3. The method of claim 1, wherein said step of sensing the temperature of said outer surface of said orthopedic implant device includes the step of measuring the temperature of said outer surface from a position external to said reaction vessel.

4. The method set forth in claim 1, wherein the step of controlling the treatment of said outer surface of said orthopedic implant device includes the step of maintaining the temperature of said outer surface substantially between 350° C. and 730° C. during at least a portion of the treatment of said outer surface.

5. The method set forth in claim 1, further comprising the additional steps of:
   a) washing said orthopedic implant device with a solvent operable to remove contaminants from said outer surface; and
   b) sputtering said outer surface of said orthopedic implant device to remove contaminants from said outer surface.

6. The method set forth in claim 1, wherein said step of treating said outer surface of said orthopedic implant device includes the steps of:
   (a) maintaining the temperature of the outer surface of said orthopedic implant device between about 350° C. and about 730° C. during at least a portion of the treatment of said outer surface; and
   (b) substantially maintaining the fatigue strength of said orthopedic implant device during treatment of said outer surface.

7. A method for increasing the wear resistance of an orthopedic implant device having a titanium-containing outer surface, comprising the steps of:
   locating said orthopedic implant device in a reaction vessel;
   raising the temperature of said outer surface of said orthopedic implant device to within a temperature range of between about 350° C. and about 730° C. which substantially maintains the fatigue strength of said orthopedic implant device;
   plasma nitriding said outer surface of said orthopedic implant device so as to nitrogen enrich said outer surface of said orthopedic implant device; and
   controlling the treatment of said outer surface of said orthopedic implant device at least partially in response to the temperature of said outer surface.

8. The method set forth in claim 7, wherein said step of controlling the treatment of said outer surface of said orthopedic implant device includes the step of using an optical pyrometer to measure the temperature of said outer surface.

9. The method of claim 7, wherein said step of controlling the treatment of said outer surface of said orthopedic implant device includes the step of measuring the temperature of said outer surface from a position external to said reaction vessel.

10. The method set forth in claim 7, further including the additional steps of:
   (a) washing said orthopedic implant device with a solvent operable to remove contaminants from said outer surface; and
   (b) sputtering said outer surface of said orthopedic implant device to remove contaminants from said outer surface.

* * * * *